United States Patent [19]

Rice

[11] Patent Number: 4,743,553
[45] Date of Patent: May 10, 1988

[54] SYNTHETIC GENES FOR BOVINE PARAINFLUENZA VIRUS

[75] Inventor: John M. Rice, Westerville, Ohio
[73] Assignee: W. R. Grace & Co., New York, N.Y.
[21] Appl. No.: 632,106
[22] Filed: Jul. 18, 1984
[51] Int. Cl.⁴ .................. C12N 1/20; C12N 15/00; C07H 21/04
[52] U.S. Cl. .................. 435/253; 435/320; 435/172.3; 536/27
[58] Field of Search .............. 435/317, 253, 172.3, 435/320; 536/27-29

[56] References Cited

U.S. PATENT DOCUMENTS

| | | | |
|---|---|---|---|
| 3,991,179 | 11/1976 | Beare et al. | 424/92 |
| 4,293,545 | 10/1981 | Kucera | 424/92 |
| 4,328,210 | 5/1982 | Kucera | 424/92 |
| 4,331,589 | 5/1982 | Hung et al. | 260/112 R |
| 4,335,106 | 6/1982 | Kucera | 424/92 |
| 4,357,421 | 11/1982 | Emtage et al. | 435/68 |
| 4,388,299 | 6/1983 | Kucera | 424/92 |
| 4,393,201 | 7/1983 | Curtis et al. | 536/27 |
| 4,415,491 | 11/1983 | Vyas | 260/112.5 R |
| 4,428,941 | 1/1984 | Galibert et al. | 260/112.5 R |

FOREIGN PATENT DOCUMENTS

82/03632 10/1982 PCT Int'l Appl.
83/03547 10/1983 PCT Int'l Appl.
83/03623 10/1983 PCT Int'l Appl.

OTHER PUBLICATIONS

Davis et al., Microbiol., pp. 1150–1154, 1973.
Gorecki et al., Proc. Natl. Acad. Sci. USA, vol. 77/pp. 3686–3690, 1980.
Amstutz, Bovine Med. & Surgery, pp. 38–47, 1980.
Lai et al., Annals N.Y. Acad. Sci., vol. 354/pp. 162–171, 1980.
Fraenkel-Conrat et al., Virology, pp. 117–139, 1982.
Rosenblatt et al., J. Virology, vol. 42, pp. 90–97, 1982.
Collins et al., Proc. Natl. Acad. Sci. USA, vol. 80, pp. 3208–3212, 1983.
Gupta et al., J. Gen. Virol., vol. 64, pp. 1679–1688, 1983.
Venkatesan, Proc. Natl. Acad. Sci., vol. 80, pp. 1280–1284, 1983.

*Primary Examiner*—Blondel Hazel
*Attorney, Agent, or Firm*—Jill H. Krafte

[57] ABSTRACT

A method is disclosed for constructing a synthetic gene for the production of a viral protein or portion thereof. The method is useful for genes found on minus-strand RNA viral genomes, such as those of rhabdoviruses or paramyxoviruses. The protein or a portion thereof prepared by expression of the synthetic gene in a suitable host may be used for vaccine or diagnostic purposes.

12 Claims, 9 Drawing Sheets

FIGURE 1 (Page 1 of 4)

```
          10        20        30        40        50        60        70
CTGCAGGGGGGGGGGGGGGGAGAACAATCATAATAAATTAATGTTGCAGGAAATAAGAAAAGAATTCGCGG
  •                                                          •••    ••
 PstI                                                       EcoRI  Fnu4HI
                                                            EcoRI*
                                                                  FnuDII
                                                              [HinfIII]

80        90       100       110       120       130       140
CAATAGACACCAAGATTCAGAGGACCTCGGATGACATTGGAACCTCAATACAGTCAGGAATAAATACAAG
  • ••          •           •         •         •
    Hinfl      AsuI         MnlI     FokI      MnlI
  MnlI         AvaII
     EcoRI*

150       160       170       180       190       200       210
ACTTCTCACAATTCAGAGTCATGTTCAAAACTATATCCCACTATCACTAACACAACAAATGTCAGATCTC
                •                                                  • • •
              Hinfl                                              BglII
                                                                   DdeI
                                                                   DpnI
                                                                   EcoRI*
                                                                   MboI
                                                                   XhoII 220       230       240       250       260       270       280
AGAAAATTTATCAATGATCTAACAAATAAAAGAGAACATCAAGAAGTGCCAATACAGAGAATGACTCATG
  •           • •                                                  •   •
 EcoRI*      DpnI                                                Hinfl
             MboI                                                  MnlI 290       300       310       320       330       340       350
ATAGAGGTATAGAACCCCTAAATCCAGACAAGTTCTGGAGGTGTACATCTGGTAACCCATCTCTAACAAG
                  •         •                 •       •
               EcoRI*     MnlI               RsaI    BstEII
```

FIGURE 1 (Page 2 of 4)

```
         360       370       380       390       400       410       420
TAGTCCTAAGATAAGGTTAATACCAGGGCCAGGTTTATTAGCAACATCTACTACAGTAACTGGCTGTATT
    ●                  ● ● ● ● ●
   Ddel               Asul
                     EcoRII  ScrFI
                             EcoRII
                             HaeIII
                     ScrFI 430       440       450       460       470       480       490
AGAATCCCATCGTTAGCAATCAATCATTTAATCTACGCTTACACCTCTAATCTTATCACCCAGGGCTGTC
 ● ●                                              ●   ●   ● ●         ●
 EcoRI*                                          HphI    EcoRII     TaqI
 HinfI                                                 MnlI  ScrFI 500       510       520       530       540       550       560
GAGATATAGGGAAATCTTACCAAGTACTACAAATAGGGATAATTACTATAAATTCGGACCTAGTACCTGA
         ●           ●   ●                       ●●    ●          ●
       EcoRI*       RsaI                               Asul       RsaI
                    [ScaI]                             AvaII
                                                     EcoRI*
                                                     [HinfIII]

570       580       590       600       610       620       630
TTTAAATCCCAGAGTCACACATACATTTAATATTGATGATAATAGGAAATCTTGCTCTCTGGCACTATTG
  ●   ●         ●                                      ●
 AhaIII   HinfI                                      EcoRI*
  EcoRI*

640       650       660       670       680       690       700
AA?ACAGATGTTT?TCAGTTATGCTCAACACCAAAAGTTGCTGAGAGATCCGATTATGCATCAACAGGTA
                                       ●   ● ●         ●          ● ●
                                      Ddel  DpnI   [AvaII]     MnlI
                                           EcoRI*              SfaNI
                                            MboI
                                            XhoII 710       720       730       740       750       760       770
TTGAGGATATTGTACTTGACATTGTCACTAATAATGGATTAATTATAACAAGAAGGTTTACAAATAATAA
          ●        ●
         RsaI    Tth111I
```

FIGURE 1 (Page 3 of 4)

```
          780       790       800       810       820       830       840
TATAACTTTTGATAAACCGTATGCAGCATTGTATCCATCAGTAGGACCAGGAATCTATTATAAGGGTAAA
                     •         •        •••••
                   Fnu4HI    BbvI     AsuI    EcoRI*
                                      AvaII  HinfI
                                      EcoRII
                                      ScrFI 850       860       870       880       890       900       910
GTTATATTTCTCGGATATGGAGGTCTAGAGCATGAAGATAACGGAGACGTAATATGTAATACAACTGGTT
            •         •  •                        •
          MnlI    [EcoPI]                        MboII
                   XbaI 920       930       940       950       960       970       980
GTCCTGGCAAAACACAGAGAGACTGTAATCAGGCTTCTTATAGCCCATGGTTCTCAAATAGGAGAATGGT
 ••                                                 •
EcoRII                                            NcoI
 ScrFI 990       1000      1010      1020      1030      1040      1050
AAACTCTATTATTGTTGTTGATAAAGGCATAGATGCAACTTTTAGCTTGAGGGTGTGGACTATTCCAATG
                        •                    •   •
                     SfaNI                     AluI
                                             MnlI 1060      1070      1080      1090      1100      1110      1120
AGCCAAAATTATTGGGGATCAGAAGGAAGATTACTTTTATTAGGTGACAGAATATACATATATACTAGAT
              •• •                        •                  • '      ••
           [BlnI]                        MboII              HphI    DpnI
            DpnI                                                    EcoRI*
            MboI                                                    MboI
                                                                    XhoII 1130      1140      1150      1160      1170      1180      1190
CCACAAGTTGGCACAGTAAATTACAGTTAGGGGTAATTGATATTTCTGATTATAATAATATAAGAATAAA
```

FIGURE 1

(Page 4 of 4)

```
       1200      1210      1220      1230      1240      1250      1260
TTGGACTTGGCATAATCTACTATCACGGCCAGGAAATGATGAATGTCCATGGGGTCATTCATGCCCAGAC
                         • • •                    •
                         Cfrl                     Ncol
                          EcoRII
                          HaeIII
                           ScrFI 1270      1280      1290      1300      1310      1320      1330
GGATGTATAACAGGAGTTTACACTGATGCATATCCGCTAAACCCATCGGGGAGTGTTGTATCATCAGTAA
         ••         •
         FokI       [AvaIII]
         SfaNI 1340      1350      1360      1370      1380      1390      1400
TTCTTGACTCACAAAAGTCTAGAGAAAACCCAATCATTACCTACTCAACAGCTACAAATAGAATAAATGA
    •         •                                         •
    HinfI     XbaI                                      AluI 1410      1420      1430      1440      1450      1460      1470
ATTAGCTATATATACAGAACACTTCCAGCTGCATATACAACAACAAATTGTATCACACATTATGATAAAG
    •         •         ••
    AluI      BbvI      AluI
                        Fnu4HI
                        NspBII
                        PvuII 1480      1490      1500      1510      1520      1530      1540
GGTATTGTTTTCATATAGTAGAAATAAATCACAGAAGTTTGAATACGTTTCAACCGATGTTATTCAAAAC 1550      1560      1570      1580      1590      1600      1610
AGAAGTTCCAAAAAACTGCAGCTAAATTGATCATCGCATATCGGATGCCAGATGACATTAAAAGAGACCA
         •••          •  •    •                         •         •
         AluI         BbvI    SfaNI                     FokI      [EcoP1]
         Fnu4HI       BclI
         PstI         DpnI
                      MboI 1620      1630      1640      1650      1660      1670
CCATACAGACAACACAGGAGATGATGCAAGATATAAAGGAATCCCCCCCCCCCCCCCTGCAGCAA
         •                             • •                   ••
         SfaNI                         EcoRI*                Fnu4HI
                                       HinfI                 PstI
```

FIGURE 2

| Sequence | Site | Position | | | | | | | |
|---|---|---|---|---|---|---|---|---|---|
| AhaIII | TTTAAA | 564 | | | | | | | |
| AluI | AGCT | 1026 | 1382 | 1406 | 1429 | 1562 | | | |
| AsuI | GGNCC | 93 | 377 | 547 | 815 | | | | |
| AvaI | GGLCC | 93 | 547 | 815 | | | | | |
| [AvaIII] | ATGCAT | 686 | 1286 | | | | | | |
| BbvI | GCAGC | 806 | 1571 | | | | | | |
| BbvI | GCTGC | 1416 | | | | | | | |
| BclI | TGATCA | 1569 | | | | | | | |
| BglII | AGATCT | 205 | | | | | | | |
| [BInI] | GGATC | 1066 | | | | | | | |
| BstEII | GGTNACC | 332 | | | | | | | |
| CfrI | QGGCCP | 1217 | | | | | | | |
| DdeI | CTNAG | 209 | 357 | 672 | | | | | |
| DpnI | GATC | 207 | 228 | 679 | 1069 | 1120 | 1571 | | |
| [EcoP1] | AGACC | 1605 | | | | | | | |
| [EcoP1] | GGTCT | 862 | | | | | | | |
| EcoRI | GAATTC | 62 | | | | | | | |
| EcoRI* | PPATQQ | 64 | 86 | 207 | 217 | 303 | 425 | 505 | 543 |
| | | 567 | 610 | 679 | 824 | 1120 | 1652 | | |
| EcoRII | CCLGG | 373 | 379 | 480 | 817 | 913 | 1219 | | |
| Fnu4HI | GCNGC | 69 | 795 | 1430 | 1560 | 1671 | | | |
| FnuDII | CGCG | 68 | | | | | | | |
| FokI | GGATG | 113 | 1275 | 1597 | | | | | |
| HaeIII | GGCC | 379 | 1219 | | | | | | |
| HinfI | GANTC | 85 | 157 | 274 | 423 | 573 | 822 | 1337 | 1650 |
| [HInfIII] | ATTCG | 63 | 542 | | | | | | |
| HphI | GGTGA | 1106 | | | | | | | |
| HphI | TCACC | 469 | | | | | | | |
| MboI | GATC | 205 | 226 | 677 | 1067 | 1118 | 1569 | | |
| MboII | GAAGA | 887 | 1089 | | | | | | |
| MnlI | CCTC | 106 | 124 | 475 | | | | | |
| MnlI | GAGG | 83 | 277 | 311 | 696 | 853 | 1022 | | |
| NcoI | CCATGG | 956 | 1238 | | | | | | |
| NspBII | CJGCKG | 1429 | | | | | | | |
| PstI | CTGCAG | 6 | 1561 | 1672 | | | | | |
| PvuII | CAGCTG | 1429 | | | | | | | |
| Rsa_ | GTAC | 325 | 516 | 555 | 714 | | | | |
| [ScaI] | AGTACT | 513 | | | | | | | |
| ScrFI | CCNGG | 375 | 381 | 482 | 819 | 915 | 1221 | | |
| SfaNI | GATGC | 1003 | 1276 | 1575 | 1624 | | | | |
| SfaNI | GCATC | 698 | | | | | | | |
| TaqI | TCGA | 490 | | | | | | | |
| Tth111I | GACNNNGTC | 722 | | | | | | | |
| XbaI | TCTAGA | 865 | 1349 | | | | | | |
| XhoII | PGATCQ | 205 | 677 | 1118 | | | | | |

FIGURE 3 (Page 1 of 3)

```
                                          27                                               54
CTG CAG GGG GGG GGG GGG GAG AAC AAT CAT AAT AAA TTA ATG TTG CAG GAA ATA
Leu Gln Gly Gly Gly Gly Glu Asn Asn His Asn Lys Leu MET Leu Gln Glu Ile 81                                              108
AGA AAA GAA TTC GCG GCA ATA GAC ACC AAG ATT CAG AGG ACC TCG GAT GAC ATT
Arg Lys Glu Phe Ala Ala Ile Asp Thr Lys Ile Gln Arg Thr Ser Asp Asp Ile 135                                              162
GGA ACC TCA ATA CAG TCA GGA ATA AAT ACA AGA CTT CTC ACA ATT CAG AGT CAT
Gly Thr Ser Ile Gln Ser Gly Ile Asn Thr Arg Leu Leu Thr Ile Gln Ser His 189                                              216
GTT CAA AAC TAT ATC CCA CTA TCA CTA ACA CAA CAA ATG TCA GAT CTC AGA AAA
Val Gln Asn Tyr Ile Pro Leu Ser Leu Thr Gln Gln MET Ser Asp Leu Arg Lys 243                                              270
TTT ATC AAT GAT CTA ACA AAT AAA AGA GAA CAT CAA GAA GTG CCA ATA CAG AGA
Phe Ile Asn Asp Leu Thr Asn Lys Arg Glu His Gln Glu Val Pro Ile Gln Arg 297                                              324
ATG ACT CAT GAT AGA GGT ATA GAA CCC CTA AAT CCA GAC AAG TTC TGG AGG TGT
MET Thr His Asp Arg Gly Ile Glu Pro Leu Asn Pro Asp Lys Phe Trp Arg Cys 351                                              378
ACA TCT GGT AAC CCA TCT CTA ACA AGT AGT CCT AAG ATA AGG TTA ATA CCA GGG
Thr Ser Gly Asn Pro Ser Leu Thr Ser Ser Pro Lys Ile Arg Leu Ile Pro Gly 405                                              432
CCA GGT TTA TTA GCA ACA TCT ACT ACA GTA ACT GGC TGT ATT AGA ATC CCA TCG
Pro Gly Leu Leu Ala Thr Ser Thr Thr Val Thr Gly Cys Ile Arg Ile Pro Ser 459                                              486
TTA GCA ATC AAT CAT TTA ATC TAC GCT TAC ACC TCT AAT CTT ATC ACC CAG GGC
Leu Ala Ile Asn His Leu Ile Tyr Ala Tyr Thr Ser Asn Leu Ile Thr Gln Gly 513                                              540
TGT CGA GAT ATA GGG AAA TCT TAC CAA GTA CTA CAA ATA GGG ATA ATT ACT ATA
Cys Arg Asp Ile Gly Lys Ser Tyr Gln Val Leu Gln Ile Gly Ile Ile Thr Ile 567                                              594
AAT TCG GAC CTA GTA CCT GAT TTA AAT CCC AGA GTC ACA CAT ACA TTT AAT ATT
Asn Ser Asp Leu Val Pro Asp Leu Asn Pro Arg Val Thr His Thr Phe Asn Ile 621                                              648
GAT GAT AAT AGG AAA TCT TGC TCT CTG GCA CTA TTG AAT ACA GAT GTT TAT CAG
Asp Asp Asn Arg Lys Ser Cys Ser Leu Ala Leu Leu Asn Thr Asp Val Tyr Gln
```

FIGURE 3    (Page 2 of 3)

```
                                   675                                          702
TTA TGC TCA ACA CCA AAA GTT GCT GAG AGA TCC GAT TAT GCA TCA ACA GGT ATT
Leu Cys Ser Thr Pro Lys Val Ala Glu Arg Ser Asp Tyr Ala Ser Thr Gly Ile 729                                          756
GAG GAT ATT GTA CTT GAC ATT GTC ACT AAT AAT GGA TTA ATT ATA ACA AGA AGG
Glu Asp Ile Val Leu Asp Ile Val Thr Asn Asn Gly Leu Ile Ile Thr Arg Arg 783                                          810
TTT ACA AAT AAT AAT ATA ACT TTT GAT AAA CCG TAT GCA GCA TTG TAT CCA TCA
Phe Thr Asn Asn Asn Ile Thr Phe Asp Lys Pro Tyr Ala Ala Leu Tyr Pro Ser 837                                          864
GTA GGA CCA GGA ATC TAT TAT AAG GGT AAA GTT ATA TTT CTC GGA TAT GGA GGT
Val Gly Pro Gly Ile Tyr Tyr Lys Gly Lys Val Ile Phe Leu Gly Tyr Gly Gly 891                                          918
CTA GAG CAT GAA GAT AAC GGA GAC GTA ATA TGT AAT ACA ACT GGT TGT CCT GGC
Leu Glu His Glu Asp Asn Gly Asp Val Ile Cys Asn Thr Thr Gly Cys Pro Gly 945                                          972
AAA ACA CAG AGA GAC TGT AAT CAG GCT TCT TAT AGC CCA TGG TTC TCA AAT AGG
Lys Thr Gln Arg Asp Cys Asn Gln Ala Ser Tyr Ser Pro Trp Phe Ser Asn Arg 999                                         1026
AGA ATG GTA AAC TCT ATT ATT GTT GTT GAT AAA GGC ATA GAT GCA ACT TTT AGC
Arg MET Val Asn Ser Ile Ile Val Val Asp Lys Gly Ile Asp Ala Thr Phe Ser 1053                                         1080
TTG AGG GTG TGG ACT ATT CCA ATG AGC CAA AAT TAT TGG GGA TCA GAA GGA AGA
Leu Arg Val Trp Thr Ile Pro MET Ser Gln Asn Tyr Trp Gly Ser Glu Gly Arg 1107                                         1134
TTA CTT TTA TTA GGT GAC AGA ATA TAC ATA TAT ACT AGA TCC ACA AGT TGG CAC
Leu Leu Leu Leu Gly Asp Arg Ile Tyr Ile Tyr Thr Arg Ser Thr Ser Trp His 1161                                         1188
AGT AAA TTA CAG TTA GGG GTA ATT GAT ATT TCT GAT TAT AAT AAT ATA AGA ATA
Ser Lys Leu Gln Leu Gly Val Ile Asp Ile Ser Asp Tyr Asn Asn Ile Arg Ile 1215                                         1242
AAT TGG ACT TGG CAT AAT CTA CTA TCA CGG CCA GGA AAT GAT GAA TGT CCA TGG
Asn Trp Thr Trp His Asn Leu Leu Ser Arg Pro Gly Asn Asp Glu Cys Pro Trp
```

FIGURE 3 (Page 3 of 3)

```
                                    1269                                        1296
GGT CAT TCA TGC CCA GAC GGA TGT ATA ACA GGA GTT TAC ACT GAT GCA TAT CCG
Gly His Ser Cys Pro Asp Gly Cys Ile Thr Gly Val Tyr Thr Asp Ala Tyr Pro 1323                                        1350
CTA AAC CCA TCG GGG AGT GTT GTA TCA TCA GTA ATT CTT GAC TCA CAA AAG TCT
Leu Asn Pro Ser Gly Ser Val Val Ser Ser Val Ile Leu Asp Ser Gln Lys Ser 1377                                        1404
AGA GAA AAC CCA ATC ATT ACC TAC TCA ACA GCT ACA AAT AGA ATA AAT GAA TTA
Arg Glu Asn Pro Ile Ile Thr Tyr Ser Thr Ala Thr Asn Arg Ile Asn Glu Leu 1431                                        1458
GCT ATA TAT ACA GAA CAC TTC CAG CTG CAT ATA CAA CAA CAA ATT GTA TCA CAC
Ala Ile Tyr Thr Glu His Phe Gln Leu His Ile Gln Gln Gln Ile Val Ser His
                                    1485                                        1512
ATT ATG ATA AAG GGT ATT GTT TTC ATA TAG TAG AAA TAA ATC ACA GAA GTT TGA
Ile MET Ile Lys Gly Ile Val Phe Ile  .   .  Lys  .  Ile Thr Glu Val  .

1539                                        1566
ATA CGT TTC AAC CGA TGT TAT TCA AAA CAG AAG TTC CAA AAA ACT GCA GCT AAA
Ile Arg Phe Asn Arg Cys Tyr Ser Lys Gln Lys Phe Gln Lys Thr Ala Ala Lys 1593                                        1620
TTG ATC ATC GCA TAT CGG ATG CCA GAT GAC ATT AAA AGA GAC CAC CAT ACA GAC
Leu Ile Ile Ala Tyr Arg MET Pro Asp Asp Ile Lys Arg Asp His His Thr Asp 1647                                        1674
AAC ACA GGA GAT GAT GCA AGA TAT AAA GGA ATC CCC CCC CCC CCC CCT GCA GCA
Asn Thr Gly Asp Asp Ala Arg Tyr Lys Gly Ile Pro Pro Pro Pro Pro Ala Ala
```

FIGURE 4

```
                                                                                   18
MET Leu Gln Glu Ile Arg Lys Glu Phe Ala Ala Ile Asp Thr Lys Ile Gln Arg
                                                                                   36
Thr Ser Asp Asp Ile Gly Thr Ser Ile Gln Ser Gly Ile Asn Thr Arg Leu Leu
                                                                                   54
Thr Ile Gln Ser His Val Gln Asn Tyr Ile Pro Leu Ser Leu Thr Gln Gln MET
                                                                                   72
Ser Asp Leu Arg Lys Phe Ile Asn Asp Leu Thr Asn Lys Arg Glu His Gln Glu
                                                                                   90
Val Pro Ile Gln Arg MET Thr His Asp Arg Gly Ile Glu Pro Leu Asn Pro Asp
                                                                                   108
Lys Phe Trp Arg Cys Thr Ser Gly Asn Pro Ser Leu Thr Ser Ser Pro Lys Ile
                                                                                   126
Arg Leu Ile Pro Gly Pro Gly Leu Leu Ala Thr Ser Thr Thr Val Thr Gly Cys
                                                                                   144
Ile Arg Ile Pro Ser Leu Ala Ile Asn His Leu Ile Tyr Ala Tyr Thr Ser Asn
                                                                                   162
Leu Ile Thr Gln Gly Cys Arg Asp Ile Gly Lys Ser Tyr Gln Val Leu Gln Ile
                                                                                   180
Gly Ile Ile Thr Ile Asn Ser Asp Leu Val Pro Asp Leu Asn Pro Arg Val Thr
                                                                                   198
His Thr Phe Asn Ile Asp Asp Asn Arg Lys Ser Cys Ser Leu Ala Leu Leu Asn
                                                                                   216
Thr Asp Val Tyr Gln Leu Cys Ser Thr Pro Lys Val Ala Glu Arg Ser Asp Tyr
                                                                                   234
Ala Ser Thr Gly Ile Glu Asp Ile Val Leu Asp Ile Val Thr Asn Asn Gly Leu
                                                                                   252
Ile Ile Thr Arg Arg Phe Thr Asn Asn Asn Ile Thr Phe Asp Lys Pro Tyr Ala
                                                                                   270
Ala Leu Tyr Pro Ser Val Gly Pro Gly Ile Tyr Tyr Lys Gly Lys Val Ile Phe
                                                                                   288
Leu Gly Tyr Gly Gly Leu Glu His Glu Asp Asn Gly Asp Val Ile Cys Asn Thr
                                                                                   306
Thr Gly Cys Pro Gly Lys Thr Gln Arg Asp Cys Asn Gln Ala Ser Tyr Ser Pro
                                                                                   324
Trp Phe Ser Asn Arg Arg MET Val Asn Ser Ile Ile Val Val Asp Lys Gly Ile
                                                                                   342
Asp Ala Thr Phe Ser Leu Arg Val Trp Thr Ile Pro MET Ser Gln Asn Tyr Trp
                                                                                   360
Gly Ser Glu Gly Arg Leu Leu Leu Leu Gly Asp Arg Ile Tyr Ile Tyr Thr Arg
                                                                                   378
Ser Thr Ser Trp His Ser Lys Leu Gln Leu Gly Val Ile Asp Ile Ser Asp Tyr
                                                                                   396
Asn Asn Ile Arg Ile Asn Trp Thr Trp His Asn Leu Leu Ser Arg Pro Gly Asn
                                                                                   414
Asp Glu Cys Pro Trp Gly His Ser Cys Pro Asp Gly Cys Ile Thr Gly Val Tyr
                                                                                   432
Thr Asp Ala Tyr Pro Leu Asn Pro Ser Gly Ser Val Val Ser Ser Val Ile Leu
                                                                                   450
Asp Ser Gln Lys Ser Arg Glu Asn Pro Ile Ile Thr Tyr Ser Thr Ala Thr Asn
                                                                                   468
Arg Ile Asn Glu Leu Ala Ile Tyr Thr Glu His Phe Gln Leu His Ile Gln Gln
                                                                                   482
Gln Ile Val Ser His Ile MET Ile Lys Gly Ile Val Phe Ile
```

SYNTHETIC GENES FOR BOVINE PARAINFLUENZA VIRUS

BACKGROUND OF THE INVENTION

This invention relates to the production of vaccines against bovine parainfluenza virus type 3 (PI-3), which is classified as a paramyxovirus. More specifically, synthetic DNA genes coding for PI-3 proteins may be produced as disclosed herein. These genes may be used for the production of the selected viral protein by transformed cells, the biosynthetic protein being useful in a vaccine, diagnostic kit or the like. The synthetic gene itself will be useful as a diagnostic agent.

Bovine parainfluenza virus type III, also called PI-3 or shipping fever virus, has considerable pathologic and economic impact as a principal factor in the initiation of an acute respiratory disease syndrome in cattle. Shipping fever syndrome can be initiated by PI-3 viral infection, usually under stressful conditions such as those associated with the shipping or feedlot management of cattle. The viral infection is believed to predispose the animals to bacterial infection, for example by *Pasteurella multocida* or *Pasteurella haemolytica*, which results in shipping fever syndrome. Annual economic losses due to diminished body weight, expensive treatments and delayed marketability are estimated in excess of $75 million. A similar virus infects sheep, leading to a respiratory disease very similar to shipping fever syndrome.

Viral vaccines, including live attenuated vaccines, have been employed for about 20 years with some success. For example, live bacterial vaccines produced from chemically modified strains of *Pasteurella multocida* and *Pasteurella haemolytica* are disclosed in U.S. Pat. No. 4,293,545 (Kucera).

The success of the viral vaccine approach for the prevention of parainfluenza viruses has been restricted by the limited effectiveness of current vaccines. This is due, in part, to interference from existing antibodies or inhibition by other viral vaccines. In addition, use of live viral vaccines on breeding animals may result in fetal infection and subsequent abortion.

Recently, it has become possible to produce a synthetic gene by formulating a bimolecular double-stranded DNA copy of a messenger RNA (mRNA) molecule. The synthetic gene produced in this manner will code for that protein which was the translation product of the selected mRNA. An example of this genetic engineering process is disclosed in U.S. Pat. No. 4,357,421 (Emtage et al.) where it is used to produce a synthetic gene for an influenza haemagglutinin protein. Influenza viruses contain no DNA; rather, they contain a segmented negative strand viral RNA (vRNA) genome which is replicated during infection to produce viral messenger RNA (mRNA) and templates for the production of further vRNA. Influenza virus genomes are of the segmented type, that is, each gene is present as a separate piece of vRNA which is transcribed separately to produce mRNAs. The process disclosed by Emtage et al. utilizes isolated vRNA as a direct template for the synthetic gene of interest.

SUMMARY OF THE INVENTION

It now is possible to construct a synthetic gene or DNA fragment which corresponds to a viral gene located on the nonsegmented, negative (or minus) strand vRNA genome of the PI-3 virus. Cells infected with the virus are obtained and the mRNA—both viral and host RNA—is separated from other cell components. Double-stranded synthetic DNA molecules complementary to the original mRNAs are constructed. This complementary DNA (cDNA) population is cloned to prepare a cDNA gene library from which viral specific genes may be selected. The viral gene of interest is identified and isolated by, for example, reciprocal hybridization and hybrid-selected translation. Once the gene of interest is identified, it is inserted into an appropriate vector which is used to transform a suitable host for expression of the gene. The expressed protein may be used to formulate subunit vaccines, diagnostic agents and the like.

It is an object of this invention to provide a method whereby synthetic genes can be constructed which correspond to genes normally found on the genomes of the bovine parainfluenza type 3 virus, a paramyxovirus.

It is a closely related object to identify and isolate the synthetic gene coding for a particular viral target protein, for example, an antigenic protein such as hemagglutinin.

It is a further object to express the selected synthetic gene in transformed hosts in order to economically manufacture the viral target protein coded for by the synthetic gene.

It is an additional object to provide a method for producing DNA sequences from which protein amino acid sequences can be determined in order to design synthetic peptides.

Moreover, it is intended that diagnostic DNA proves and peptide diagnostic agents be provided by using the process of this invention.

The following abbreviations have been used throughout in describing the invention:

bp—base pairs
BSA—bovine serum albumin
cDNA—complementary DNA
Ci—curie
cm—centimeter
dATP—deoxy-adenosine triphosphate
dCTP—deoxy-cytidine triphosphate
dGTP—deoxy-guanosine triphosphate
dTTP—deoxy-thymidine triphosphate
DTT—dithiothreitol
DNA—deoxyribonucleic acid
EDTA—ethylenediaminetetraacetic acid
GuSCN—guanidine thiocyanate
HA—hemagglutinin
HEPES—N-2-hydroxyethylpiperazine-N'-2-ethane sulfonic acid
IU—International unit
M—mole
MDBK—Madin-Darby bovine kidney (cells)
MET—methionine
$\mu$—micro
mM—millimole
mRNA—messenger RNA
NC—nucleocapsid protein
oligo(dA)—polymer made up of a few (usually 2-20) deoxyadenosine molecules
oligo(dT)—polymer made up of a few (usually 2-20) deoxythymidine molecules
$^{32}$P—radioactive phosphorus, mass no. 32
%—percent
PI-3—bovine parainfluenza virus type 3
PIPES—piperazine-N,N'-bis[2-ethane sulfonic acid]
poly-A—poly-deoxyadenosine
poly-C—poly-deoxycytidine poly-G—poly-deoxyguanosine
RNA—ribonucleic acid
rRNA—ribosomal RNA
SDS—sodium dodecylsulfate
SSC—0.15 M sodium chloride - 0.015 sodium citrate (pH 7.0)
TNE—10 mM Tris-HCl (pH 8.0) - 100 mM sodium chloride - 1.0 mM EDTA (pH 8.0)
Tris-HCl—Tris(hydroxymethyl)aminomethane-HCl
tRNA—transfer RNA
U—unit
v/v—volume/volume
vRNA—viral RNA
w/v—weight/volume
X—any amino acid residue

BRIEF DESCRIPTION OF THE DRAWINGS

FIG. 1, in four parts, is a representation of the DNA sequence of the bovine parainfluenza virus hemagglutinin (HA) cDNA cloned by the method of this invention, including the restriction enzyme cleavage sites.

FIG. 2 is a table listing the restriction enzyme sites in the cloned cDNA of FIG. 1.

FIG. 3 is a translation of the DNA sequence of the HA cDNA gene of FIG. 1 into the corresponding amino acid sequence.

FIG. 4 is the predicted amino acid sequence of the HA protein which will be the translation product of the HA cDNA gene of FIG. 1.

DESCRIPTION OF THE INVENTION

In this description of the invention, references to "mRNA" and "cDNA" are meant to refer to the whole RNA or DNA molecule, respectively, or to any biologically significant portion thereof. That is, it is intended that the method of this invention be practiced either with respect to a complete viral mRNA molecule or with respect to a sub-portion of the viral mRNA molecule. For example, it may be desired to isolate, copy and clone only that portion of a viral gene which codes for a particular protein subunit or portion thereof, or for a particular antigenic site.

PI-3 virus is classified as a paramyxovirus on the basis of morphological, serological and biochemical properties. Paramyxoviruses are "RNA viruses" and contain no DNA. Their genetic information is contained solely in a single-stranded, continuous (or non-segmented) piece of RNA. Members of the paramyxovirus family exhibit a replication strategy based on a negative stranded RNA genome. The general scheme of paramyxovirus RNA replication entails the transcription of subgenomic mRNA species from the negative-stranded template from a single promotor by a virion-associated transcriptase complex. In those systems which have been studied, each mRNA species is associated with polyribosomes, is polyadenylated and generally encodes a single viral protein.

The replication of PI-3 has received little study, although several viral structural proteins have been identified. See, for example, Shibuta et al., "Characterization of Bovine Parainfluenza Virus Type 3," *Microbiol. Immunol.*, Vol. 23, pp. 617-28 (1979) and Guskey et al., "High Yield Growth and Purification of Human Parainfluenza Type 3 Virus and Initial Analysis of Viral Structural Proteins," *J. Gen. Virology*, Vol. 54, pp. 115-23 (1981). The prior art discloses no information regarding the intracellular proteins or the viral mRNA species synthesized during viral replication. Moreover, transcription and coding assignments for the PI-3 mRNAs are not available, except as disclosed herein.

The invention disclosed herein enables one to construct a discrete synthetic gene or DNA fragment corresponding to a gene located on the nonsegmented, minus strand vRNA genome of the PI-3 virus. The synthetic gene or fragment codes for a PI-3 viral protein or portion thereof and comprises a double-stranded DNA gene which is a copy of the viral RNA gene coding for that protein or portion thereof. The synthetic gene may be used for the production of the protein of interest, or "target" protein. "Target" protein will be used herein to designate both the viral protein of interest and the protein produced by the expression of the synthetic gene. It should be understood, however, that the expressed protein may differ in insignificant ways from the viral protein, or may correspond to only a portion or subunit of the viral protein.

As a preliminary step to constructing a synthetic gene, the target protein is identified. Where preparation of a subunit vaccine or diagnostic agent is desired, the target protein may be identified by demonstrating that it can stimulate the formation of neutralizing or protective antibodies by an infected animal. In the case of the PI-3 virus, viral hemagglutinin (HA) is the principal structural protein against which protective antibodies are generated. The HA protein is found on the surface of the virus and is responsible for attachment of the virus to the cells for initiation of the infection process. Isolation of the gene coding for the hemagglutinin protein is desired so that it can be cloned and used for the extraviral production of the HA protein. This biosynthetic HA protein is particularly suitable for use in vaccines. It will stimulate the production of antibodies against PI-3 in vaccinated animals without risking viral infection because the HA protein itself is not infectious. However, there is evidence that other structural proteins also may contribute to the triggering of antibodies. The activity of a vaccine or diagnostic agent can be futher enhanced by the inclusion of biosynthetic versions of these other structural proteins. For example, structural fusion protein, which is a viral surface protein responsible for fusion to the cell to be infected and having properties which cause transfer of the viral RNA to those cells, may be desired for inclusion in a vaccine or the like.

Host cells infected with the virus are obtained by conventional means. It is preferred that Madin-Darby bovine kidney (MDBK) cells be used as the host cells, since they support high levels of viral replication. The cells are infected with the virus and prepared according to standard cell culture techniques.

The RNA is harvested from the cells by any convenient means. For example, the guanidine thiocyanate-CsCl method of Chirgwin et al., Biochemistry, Vol. 18, pp. 5294–99 (1979), which is described in more detail in Example I, may be used. Total RNA, that is the host mRNA, tRNA and rRNA as well as viral vRNA and mRNA, is isolated or recovered.

The mRNA of all viruses infecting eukaryotes naturally occurs in polyadenylated (poly-A-tailed) form. It is preferred to take advantage of this in separating mRNA from other cell components and from other RNAs. To isolate polyadenylated mRNA, the total recovered RNA most conveniently is fractionated on oligo(dT) cellulose columns. However, other methods may be used to separate the mRNA, if desired.

From polyadenylated mRNAs, it is possible to construct double-stranded hybrid RNA/DNA molecules using the technique of reverse transcription. The enzyme reverse transcriptase, an RNA-directed DNA polymerase, will synthesize, on each molecule, a new strand of DNA complementary to the existing strand of RNA. This transcription requires the presence of a double-stranded growing point or primer where transcription may begin. The primer may be constructed by hybridizing an oligo(dT) molecule to the 3'-poly-A end of the mRNA. The reverse transcriptase begins synthesizing cDNA at the double-stranded growing point, producing the double-stranded mRNA/cDNA hybrid molecule.

Next, the mRNA strand of each double-stranded molecule is digested or removed in a manner which leaves the cDNA strand intact. For example, the RNA strand may be digested by alkaline hydrolysis or with ribonuclease, or removed from the cDNA strands by heat denaturation. The result is single-stranded cDNA, which is a self-priming structure with a hairpin loop at its 3' end.

The single-stranded cDNA molecules are converted into double-stranded cDNA by using reverse transcriptase or another DNA polymerase, such as E. coli DNA polymerase (E.C. 2.7.7.7), or using a Klenow fragment of a DNA polymerase (formed by cleaving the polymerase molecule with trypsin). Any of these enzymes will construct a second DNA strand complementary to the first single-strand cDNA molecule, with transcription beginning at the partially double-stranded hairpin end primer. The resulting molecule is substantially double-stranded cDNA, with a remaining single-stranded hairpin end. By treating the molecules with S1 nuclease (E.C. 3.1.30.1), a single-strand specific nuclease, the single-stranded hairpin end is trimmed. The result is a population of double-stranded cDNA molecules which are complementary to the original population of mRNA molecules.

It should be remembered that the RNA molecules used as templates in this process comprise both viral and host mRNAs. As a result, the cDNA population prepared by the method described above is quite heterogeneous. The cDNAs are cloned to generate a library or gene bank from which the cDNA gene of interest can be identified.

The cDNA clone library is prepared by inserting the cDNA genes into suitable vectors for transformation of suitable hosts. Host-vector combinations for this stage of the procedure should be chosen for ease in manipulation and consistency of excision. In addition, the vector should contain a single restriction endonuclease recognition site which preferably is suitable for being reformed by homopolymeric tailing of the cDNA and the digested vector. For example, the plasmid vector pBR322, suitable for transforming E. coli, may be digested with Pst I restriction endonuclease (E.C. 3.1.23.31) to produce a linear DNA molecule. This linear molecule may be tailed using terminal deoxynucleotidyl transferase (E.C. 2.7.7.31) and dGTP to yield poly-G tails on the vector. Poly-C tails may be added to the cDNA molecules using terminal deoxynucleotidyl transferase and dCTP. The poly-G tails on the vector are complementary to the poly-C tails on the cDNAs.

The products (in this embodiment, poly-C tailed cDNAs and poly-G tailed linear vectors) then may be mixed and annealed by heating and slowly cooling to form reconstituted plasmids having the cDNA genes inserted at the original Pst I restriction site. Upon annealing, one strand at each end of the inserted cDNA will have a gap corresponding to the Pst I site. Once the recombinant plasmid is introduced into a transformation host cell, the host will repair the gaps, reconstructing the Pst I site at either end of the inserted gene. This construction permits the subsequent excision of the cDNA gene by the use of Pst I restriction endonuclease for further manipulation.

There are alternative procedures which can be used to insert the cDNA genes into vectors. For example, it is possible to join the fragments with linker molecules using an appropriate DNA ligase. Alternatively, homopolymeric tailing may be used to create complementary poly-A and poly-T sequences at the ends of each fragment.

The chimeric plasmids or vectors thus constructed are used to transform cells suitable for transformation by the vector utilized. E. coli is particularly well suited as a transformation host, but other organisms, Bacillus subtilis, for example, may be used with appropriate vector selection. From the cDNA clone library thus constructed, clones containing viral-specific genes may be identified and isolated.

A sub-clone bank comprising only viral specific clones, that is, transformed host cells which comprise viral specific gene or DNA fragments, is formed using the technique of differential hybridization. Single stranded cDNA probes are prepared from viral-infected and from uninfected MDBK cells by the method described above, except that $^{32}P$ dCTP is used in order to obtain radiolabeled cDNA. Cloned E. coli cells from the cDNA library previously constructed are grown on nitrocellulose filters and duplicate filters are prepared. The colonies are lysed and the released nucleic acid fixed to the filters. The radiolabeled probes are hybridized to the cloned cDNA on the filters. After unbound probe is removed, viral specific colonies, that is, colonies comprising cDNA corresponding to a viral gene, may be identified using autoradiography. Positive colonies which read positive only on filters hybridized using the cellular-plus-viral cDNA probe, and not on the duplicate filters hybridized using the cellular mRNA probe, are viral-specific cDNA clones. Only these clones need be studied in the identification processes described below.

In order to facilitate the screening process, reciprocal hybridization (or colony cross-hybridization) analysis may be conducted to define individual groups of clones within the viral-specific cDNA clone library which correspond to separate viral genes. This step is not required since identification can be made by transformation and direct expression, followed by immunologic identification using, for example, monoclonal antibodies. However, since there may be large numbers of clones in the library, it will be more efficient to streamline the process by creating groups of clones which cross-hybridize within the group and therefore are considered to contain segments of the same viral gene.

In reciprocal hybridization, a single viral-specific clone is digested with Pst I to release the cDNA insert. The insert then is separated, radiolabeled with $^{32}P$, and hybridized against all the clones in the PI-3 cDNA library. All clones hybridizing with the probe are designated Group A. A second probe is derived from one of the nonhybridizing clones and the procedure repeated to form Group B, etc., until multiple groups are formed, and the clones are grouped to the extent possible or desired. In the PI-3 virus embodiment discussed herein, Groups A and C contained the largest number of clones and, based on analogy to mRNA abundance patterns of other paramyxoviruses (Rozenblatt et al., "Cloning and Characterization of DNA Complementary to the Measles Virus mRNA Encloding Hemagglutinin and Matrix Protein," *J. Virology*, Vol. 42, pp. 790–97 (1982)), these groups were presumed to encode the viral nucleocapsid protein gene and the HA protein gene, respectively, as shown in Table I.

Northern blot analysis may be used to determine the coding assignments of each of the clone groups, using a prototype clone from each group. By this technique, the clones may be correlated to the corresponding progenitor mRNAs. Individual prototype clones are radiolabeled and used as probes to detect viral mRNAs from infected cells which have been blotted to nitrocellulose filters. The viral mRNAs may be given tentative coding assignments based on the similarities of size relationships to virion proteins and to mRNAs of other related viruses, as determined, for example, by electrophoresis. Six distinct poly-A RNA species, designated RNA 1-6, are found in PI-3 infected but not mock-infected cells. Mock-infected cells are prepared according to the same procedures as viral-infected cells, without the addition of the viral agent. Using vesicular stomatitis virus mRNAs, or other mRNAs of known size, as markers, the molecular weights of the PI-3 mRNAs may be estimated.

As shown in Table I, the coding capacity of the six PI-3 poly-A RNA species correlates roughly with the sizes of the six viral structural proteins and with the estimated total coding capacity of the viral genome. The Group A probe (mRNA 1) hybridized at a position corresponding to the putative nucleocapsid mRNA and the Group C probe (mRNA 3) hybridized at a position corresponding to the putative HA mRNA. No hybridization to mRNA from uninfected host cells (i.e., host mRNA) was observed.

Hybrid-selection and in vitro translation of viral mRNA may be used to confirm coding assignments and thus definitively identify individual clones encoding the viral target protein, e.g., the HA protein. By these procedures, poly-A mRNAs from viral-infected and control cells can be compared for their ability to direct viral-specific protein synthesis in a mRNA-dependent cell-free translation system.

Plasmid cDNA from clones in each group are isolated and immobilized on nitrocellulose filters. Poly-A mRNAs derived from virus-infected or mock-infected (control) cells are hybridized with the filter-bound cDNA. The mRNAs which specifically hybridize to each of the immobilized cDNAs are eluted from the filters and translated in vitro. Analysis of the translation products by a technique such as polyacrylamide gel electrophoresis (PAGE) may be used to confirm the identification of the clones with respect to the viral protein encoded by the cDNA of each clone Group. It may be desired also to use immunologic analysis of the in vitro expressed proteins because proteins which are glycosylated when produced in vivo will not be glycosylated in vitro and therefore will not migrate to the same positions on the gel. In the PI-3 embodiment, the Group A clones select mRNA which directs the synthesis of a protein which migrates with the PI-3 nucleocapsid protein; Group C clones select mRNA which directs synthesis of a protein migrating with the HA protein. No viral-specific proteins should be detectable in extracts of the translation products of mRNAs from the mock-infected control cells.

Next, the clone encoding the target protein may be characterized by restriction enzyme analysis and/or nucleotide sequence determination. This step will be of particular interest and importance if it is desired to construct a gene encoding only a particular portion of the target protein, such as the portion containing an active antigenic site on the protein. Alternatively, this information may be used to design and construct a synthetic protein corresponding to the active site of the target protein, or for the study and rational design of antiviral drugs. These characterization procedures are carried out by conventional methods and techniques. The FIGURES show the results of the characterization of the PI-3 HA gene. FIG. 1 is a representation of the DNA sequence of the gene cloned as described above. FIG. 2, which lists the restriction enzyme sites of the gene, FIG. 3, a translation of the DNA sequence of the HA gene, and FIG. 4, the predicted amino acid sequence of the HA protein which will be formed, were generated by computer analysis of the DNA sequence of the gene.

Referring to FIG. 1, the DNA sequence and restriction enzyme recognition and cleavage sites are fully detailed. By convention, the DNA sequence is read in a 5' to 3' direction. The HA cDNA insert shown in this FIGURE is 1675 base pairs in length, including the poly-G and poly-C tails used for cloning. Without the tails, this cDNA clone represents 1633 bases derived from the PI-3 HA mRNA. The clone represents a substantially complete cDNA copy of the HA mRNA; primer extension sequencing of the HA mRNA obtained from infected cells indicates that only about 10 to 15 bases are missing at the 5' end of the gene. In the gene of FIG. 1, the first translation initiation codon (ATG) encoding a methionine (MET) residue is found at position 40 in the sequence. A double stop codon (TAG TAG) has been identified near the 3' end of the cloned gene (position 1486). It is therefore apparent that FIG. 1 represents a nearly complete copy of the viral HA mRNA and probably all of the protein coding region of that mRNA.

While another initiation codon may exist further upstream in the viral mRNA, and thus is not indicated in FIG. 1, that is unlikely. Most eukaryotic viral mRNAs are characterized by the presence of a 5' non-coding stretch of bases which contain the ribosome binding site of the mRNA. The putative non-coding 5'-sequence of the gene shown in FIG. 1 is approximately 40 bases long. In addition, as mentioned above, about 10 to 15 mRNA bases are believed to be missing from the cDNA sequence.

The non-coding 3'-sequence is characterized by a canonical polyadenylation signal (AAATAA) at position 1492 in the DNA sequence, immediately following the double stop codon. This sequence (underlined in FIG. 1) signals the addition of poly-A tails to mRNAs in vivo.

FIG. 2 is a listing of all possible restriction enzyme or endonuclease sites in the cloned cDNA gene of FIG. 1. The data in the list was generated by computer analysis of the DNA sequence. The first column indicates the restriction enzyme abbreviation. The second column is the recognition or cleavage site for the enzyme and the third column provides the location, by base number, of each enzyme in the sequence. The numbers represent the 5' side of the cleavage site unless the enzyme abbreviation is in brackets. The brackets indicate that only a recognition site for that particular enzyme is known; the enzyme actually may cleave at a different site. The letters designating the recognition or cleavage site represent the following amino acids:

A—adenine
C—cytosine
G—guanine
J—adenine or cytosine
K—guanine or thymine
L—adenine or thymine
M—cytosine or guanine
N—adenine, cytosine, guanine or thymine
P—adenine or guanine
Q—cytosine or thymine
T—thymine FIG. 3 indicates the translation of the DNA sequence of FIG. 1 into the corresponding amino acid sequence. By convention, the amino acid sequence is read from amino terminus to carboxyl terminus. The cDNA clone shown in FIG. 1 is characterized by one open translation reading frame from position 1 through position 1485 of the DNA sequence where a double stop codon is found. All other reading frames are blocked by the presence of multiple stop codons throughout the sequence.

Measured from the first methionine residue at nucleotide postion 40 (in FIG. 3) to the termination or stop codons at position 1486, the polypeptide encoded by this cDNA gene contains a predicted 482 amino acid residues (shown in FIG. 4) and has a predicted molecular weight of 54,142 daltons. This value is less than the observed molecular weight of HA protein separated from virions, which is as would be expected in the absence of glycosylation. Shown in FIG. 4 is the predicted amino acid sequence of the HA polypeptide (the target protein) with the putative glycosylation sites (Asn-X-Ser or Asn-X-Thr) underscored with a solid line.

Hydropathicity analysis has revealed several hydrophilic and hydrophobic domains within the protein. Of importance is the hydrophobic domain at the extreme carboxyl terminus (residues 455 to 482) of the protein which is characteristic of membrane proteins such as viral hemaglutinins. This terminal hydrophobic sequence is indicated by broken underscoring in FIG. 4.

Having identified the cDNA gene for the target protein, the gene then is inserted into an appropriate expression vector. Criteria for the selection or construction of an appropriate vector for this purpose will depend on specific process requirements (e.g., purification, yield), product stability (i.e., susceptibility to proteases, etc.), and product toxicity or inhibition. The choice of expression vector and host will be within the knowledge and skill of a person working in this art.

In assessing the appropriateness of the vector for expression of the cDNA gene, a suitable means of detecting expression of the target protein must be employed. Various standard immunoassay methods may be used, with detection of the target protein either by colorimetry or autoradiography. Monoclonal antibodies may be prepared, either against the purified target protein or the virus of interest, i.e., against each of the proteins of the virus, for use in the immunoassay.

The recombinant plasmids, formed by inserting the cDNA gene of interest into the selected expression vector, are used to transform hosts, which then are cloned. It is intended that the target will accumulate protein when the transformed hosts are cultured in a suitable medium under suitable conditions. The medium and conditions will depend on the transformation host and selection will be within the knowledge and skill of a person working in this art. The protein expression product will be encoded by the cloned synthetic gene, under the influence of the adjacent promoter region of the plasmid. The vector preferably will have been engineered or selected to include a strong promoter for maximal expression of the gene of interest. The expressed protein may be identical or substantially identical to the viral protein of interest, may represent a portion of that protein, or may be a translation fusion protein. In this context, a "translation fusion protein" is a peptide which is the product of the expression of two fused genes or segments thereof, that is, fused translation products. A translation fusion protein produced by the method of this invention will comprise all or part of the viral target protein and an amino acid sequence from a gene located adjacent to the gene of interest on the transformaton vector or host DNA. The translation fusion protein can be expected to be immunologically active.

The protein product may be harvested by conventional means. For example, the host cells may be centrifuged and lysed, or supernatant containing excreted protein may be collected. The protein may be isolated or purified from the lysate or supernatant by molecular sieve chromatography, high pressure liquid chromatography, or immunoaffinity chromatography. Monoclonal antibodies specific for the target protein may be used in the latter purification method.

The purified polypeptide will be antigenic and may be used as a vaccine. When administered as a vaccine, in a suitable adjuvant, the biosynthetic antigen will elicit production of antibodies to the target protein in the treated animal or human, thus offering protection against infection by the virus. Typically, vaccines are administered by subcutaneous or intramuscular injection, intravenously, orally or by aerosol.

The cDNA itself will be useful in assays to detect the presence of the corresponding virus in various environments, such as the blood of an animal thought to be infected. For example, the animal's mRNA may be isolated and immobilized on a solid support. Incubation with cDNA for the target virus or target protein will cause the labeled viral cDNA probe to bind to the test mRNA, if viral mRNA is present. Bound cDNA can be detected, e.g., by colorimetry, autoradiography, etc., after unbound cDNA is removed.

Moreover, it will be possible to design and construct synthetic peptides based on knowledge of the nucleotide sequence of a cDNA gene constructed according to the method of this invention. The nucleotide sequence of the gene can be translated into the corresponding amino acid sequence of the expression protein, as in FIGS. 3 and 4. The protein itself may be synthesized chemically, or a smaller peptide may be designed and synthesized which will incorporate one or more active or antigenic sites of the trget protein.

The Examples which follow are given for illustrative purposes only and are not meant to limit the invention described herein.

The stock solutions and culture media used in the Examples were prepared as indicated below.

First Strand cDNA Synthesis Medium

| | |
|---|---|
| Tris-HCl (pH 8.3) | 0.01 M |
| Potassium chloride | 60.00 mM |
| Magnesium chloride | 10.00 mM |
| dCTP | 0.50 mM |
| dATP | 0.50 mM |
| dGTP | 0.50 mM |
| dTTP | 0.50 mM |
| DTT | 10.00 µg |
| Oligo(dT) (12-18) | 5.00 µg/ml |

Second Strand cDNA Synthesis Medium

| | |
|---|---|
| HEPES (pH 6.8) | 0.20 mM |
| Potassium chloride | 60.00 mM |
| dCTP | 0.50 mM |
| dATP | 0.50 mM |
| dGTP | 0.50 mM |
| dTTP | 0.50 mM |

Denhardt's Solution

| | |
|---|---|
| Ficoll (TM) (Pharmacacia Fine Chemicals, Inc.) | 5.0 g |
| Polyvinylpyrrolidone | 5.0 g |
| BSA (Pentax Fraction V) | 5.0 g |
| $H_2O$ | To 500 ml |

Filter through a disposable Nalgene filter. Store at $-20°$ C.

EXAMPLE I (Isolation of Host and Viral mRNAs)

Stock Virus Preparation: Madin-Darby bovine kidney (MDBK) cells obtained from the American Type Culture Collection (ATCC), 12301 Parklawn Avenue, Rockville, Maryland 30852, were grown in Minimum Essential Medium (Modified) (Dulbecco's Modification) ("DMEM") (Flow Laboratories, Inc.) supplemented with 10% fetal calf serum (K.C. Biologicals). Bovine parainfluenza virus type 3 (Strain SF-4, VR-281, obtained from ATCC) was plaque purified twice. Virus stocks prepared by infecting MDBK cells with a virus-saline solution at a low multiplicity of infection ($<0.01$ PFU/cell). The infected cells were grown in DMEM at $37°$ C. for about 3 to 4 days until cytopathalogy was nearly complete, and virus-containing supernatants harvested, aliquoted and frozen at $-70°$ C. until use. Stocks were titrated by plaque assay on MDBK cells under a semisolid overlay of 2.0% (w/v) methylcellulose (Dow Chemical Co.) in DMEM supplemented with 2% fetal calf serum, 50 I.U./ml penicillin and 50 µg/ml streptomycin. Visible plaques appeared in three days, at which time plates were stained with crystal violet and the plaques counted.

Preparation of Tritiated PI-3 mRNA: In T-150 flasks containing infected MDBK cells, the RNA was labeled metabolically with 20 uCi per ml $^3$H-uridine in the presence of 1.0 µg actinomycin D per ml at 18 hours post-infection, the peak period of viral mRNA synthesis. The actinomycin D is used to prevent transcription of host DNA to RNA while allowing transcription of vRNA to viral mRNA, with the result that only viral mRNA becomes labelled. Tritiated PI-3 mRNAs were used as comparisons in the Northern blot analysis and to define the sizes of the PI-3 messages.

Isolation of RNA: Total RNA was harvested from the infected MDBK cells using the guanidine thiocyanate-cesium chloride method of Chirgwin et al., Biochemistry, Vol. 18, pp. 5294-99 (1979). Pursuant to this method, $10^8$ from five T-150 flasks were lysed in situ by the addition of 10 ml of guanidine thiocyanate (GuSCN) buffer (5.0 M GuSCN, 50.0 mM Tris-HCl (pH 7.0), 50.0 mM EDTA, 5% (v/v) B-mercaptoethanol) adjusted to 2% (w/v) with Sarkosyl-40 (TM) (Ciba-Geigy Corp.). This mixture was heated to $55°$ C. for 5 minutes and then briefly chilled on ice for 5 minutes. The lysate was layered over 7.0 ml of 5.7 M CsCl in 50 mM EDTA and centrifuged at $20°$ C. for 5 hours at 15,000 x g in a swinging bucket rotor (25,000 RPM). Total RNA was recovered as a pellet from the bottom of the centrifuge tube. The RNA pellet was subjected to further fractionation on oligo(dT) cellulose columns to isolate poly-A-containing mRNA according to the method of Aviv and Leder, Proc. Natl. Acad. Sci. USA, Vol. 69, pp. 1408-12 (1972).

RNA was isolated from mock-infected MDBK cells in the same manner except that the cells are "infected" with saline, rather than a virus-saline solution. RNA isolated from mock-infected cells was used for comparative purposes in Examples IV and V.

EXAMPLE II (Synthesis of cDNA Molecules)

DNA complementary to the poly-A mRNA isolated in Example I was synthesized by incubating 5.0 µg poly-A mRNA in 100 µl First Strand cDNA Synthesis Medium at $37°$ C. for 10 minutes. Next, 12 U avian myeloblastosis virus reverse transcriptase (Life Sciences, Inc.) per µg mRNA was added. This mixture was incubated at $42°$ C. for 45 minutes, chilled on ice for 5 minutes and heated to $100°$ C. for 3 minutes. It was centrifuged at 15,000 x g in a microfuge for 2 minutes to remove precipitated protein.

Double-stranded cDNA was synthesized from single-stranded cDNA in a 200 µl incubation containing 100 µl first strand reaction supernatant in 100 µl Second Strand cDNA Synthesis Medium. A volume of E. coli DNA polymerase (Klenow fragment) was added to obtain a concentration of 10 U per µg of single-stranded cDNA. This mixture was incubated for 16 hours at $15°$ C. The reaction was stopped by performing a single phenol-chloroform extraction.

The products (double-stranded cDNA molecules) were desalted and concentrated by two sequential spermine precipitations followed by ethanol precipitation. Double-stranded cDNA in the second-strand reaction solution was precipitated in the presence of 10 mM spermine at $0°$ C. (on ice) for 30 minutes. The precipitated cDNA was collected by centrifugation at 15,000 x g in a microfuge for 5.0 minutes. The pellet was resuspended in a solution containing 10 mM spermine. After a 30 minute incubation at $0°$ C., the precipitate was collected by centrifugation as before. Precipitated cDNA was resuspended in 400 mM sodium acetate and 10 mM magnesium acetate before being precipitated with 2.5 volumes ethanol at $-70°$ C.

The double-stranded cDNA products were digested with S1 nuclease to remove the single-stranded hairpin end. The cDNA was incubated in a 50 µl volume of 0.3 M NaCl, 0.03 M sodium acetate, 0.003 M $ZnCl_2$ (pH 4.5), and 10 U S1 nuclease for 30 minutes at 37° C. The double-stranded cDNA reaction products were desalted and concentrated by spermine precipitation.

EXAMPLE III (Construction of cDNA Library)

The population of cDNAs prepared from mRNA from viral-infected cells in Example II was tailed by incubating with 30 U terminal deoxynucleotidyl transferase, in a reaction buffer containing 250 mM potassium cacodylate (pH 7.2), 2.0 mM $CoCl_2$, 1.0 mM DTT and 1.0 mM dCTP for 15 minutes at 25° C. to produce cDNA molecules with poly-C tails. The plasmid vector pBR322 was digested with Pst I restriction endonuclease at 32° C. for 16 hours to produce linear DNA molecules. These linear molecules were poly-G tailed using dGTP by the same prodecure used to tail the cDNAs. The poly-G-tailed vector molecules were mixed with the poly-C-tailed cDNAs and annealed by incubating as follows: 70° C. for 30 minutes, 37° C. for 150 minutes and 22° C. for 30 minutes, in order to form reconstituted plasmids having the cDNA genes inserted at the original Pst I restriction site. This construction permits subsequent excision of the cDNA genes by Pst I. The chimeric plasmids created in this Example were used to transform E. coli K-12 strain AC80 (donated by L. Bopp, General Electric) cells by the calcium phosphate coprecipitation method described by Kushner, Proc. of the Int'l Symposium of Gen. Eng., Biomedical Press (1978). The transformed E. coli cells constituted a library of cells containing the cDNA inserts.

EXAMPLE IV (Identification of Viral-Specific Clones)

Clones comprising viral-specific genes were identified by differential colony hybridizations using $^{32}P$-labeled cDNA probes derived by reverse transcription of mRNA which was extracted by the procedure of Example I from either PI-3 virus infected or mock-infected MDBK cells. Synthesis of the radiolabeled single-stranded cDNA probes was conducted by the method described in Example II except that $^{32}P$ dCTP was substituted for dCTP in the reaction mixture.

The cloned E. coli cells prepared in Example III were grown on nitrocellulose filters overlaid onto Luria agar plates. Duplicates of each filter were prepared. The resulting colonies were lysed using 0.5 M NaOH, and the released nucleic acid was fixed to the filters by heating for 60 minutes at 80° C. in a vacuum oven. The filters containing the lysed E. coli colonies were prehybridized by incubating in 5x Denhardt's Reagent (that is, at five times the concentration given above), 5x SSC, 100 μg/ml denatured salmon sperm, 50% formamide and DNA for 24 hours at 42° C.

Hybridization of the radiolabeled probes to the cloned cDNA was conducted by incubating the filters in 2x Denhardt's Reagent, 5x SSC, 50 μg/ml salmon sperm DNA, 50% formamide, 7.5% dextran sulfate, and radiolabeled probe specific for either MDBK mRNA or for MDBK-plus-PI-3 mRNA. Incubation was for 24 hours at 42° C. Unbound probe was removed by washing the filters in 2x SSC plus 0.1% SDS, followed by washing in 0.1x SSC with 0.1% SDS. Viral-specific clones were detected using autoradiography. Colonies hybridizing differentially with probes containing viral sequences, that is, positive only on filters hybridized using the MDBK-plus-PI-3 mRNA probes, and negative on the duplicate filters hybridized using the MDBK mRNA probes, were selected and rescreened to confirm viral specificity.

EXAMPLE V (Reciprocal Hybridization)

The viral-specific cDNA clones of Example IV were grouped by the reciprocal hybridization method of Rozenblatt et al., "Cloning and Characterization of DNA Complementary to the Measles Virus mRNA Encoding Hemagglutinin and Matrix Protein," J. Virology, Vol. 42, pp. 790-97 (1982). Cloned DNA was excised from the pBR322 vehicle of one of the viral-specific cDNA clones by digesting with Pst I restriction enzyme. The restricted DNA was resolved by fractionation in 1.5% agarose gel, yielding linear pBR322 plasmid DNA and insert cDNA. The insert cDNA was electroeluted from the gel and radiolabeled with $^{32}P$-dCTP by the nick-translation procedure of Maniatis et al., Proc. Natl. Acad. Sci, U.S.A., Vol. 72, pp. 1184-88 (1975), using The Nick Translation Reagent Kit available from Bethesda Research Laboratories.

The radiolabeled cDNA probe was used as a hybridization probe against all the viral-specific clones in the PI-3 cDNA library in the following manner: The colonies were simaltaneously consolidated onto a master agar plate and a nitrocellulose filter on a second agar plate and allowed to grow. The colonies on the filter were lysed with alkali by the method of Hanahan and Meselson, Gene, Vol. 10, pp. 63-67 (1980). After neutralization, the DNA was fixed onto the filter by baking. These colony DNA blots were hybridized with the $^{32}P$-probe as described by Grunstein and Hogness, Proc. Natl. Acad. Sci. U.S.A., Vol. 72, pp. 3961-65 (1975). Following hybridization, the filters were autoradiographed. Those clones hybridizing with the labeled probe were designated PI-3 Group A.

A second probe was prepared in the same manner from the nonhybridizing group. The hybridization procedure was repeated until all the clones had been subdivided into six classes based upon the reciprocal hybridization analysis. Table I indicates the number of clones in each group, the approximate size of the cDNA insert, approximate size of corresponding mRNA, molecular weight of mRNA and the tentative coding assignment, where known.

TABLE I (Classification of PI-3 cDNA Clones Based Upon Reciprocal Hybridization Relationships)

| Group Number: | A | B | C | D | E |
|---|---|---|---|---|---|
| Probe[1] | 6-8 | 5-2 | 3-5 | 5-4 | 6-6 |
| Number of Clones | 38 | 8 | 10 | 3 | 5 |
| Size Range of Inserts | 500–1500bp | 400–1300bp | 500–1600bp | 400–1300bp | 500–1000bp |
| Corresponding mRNA | RNA 5 | RNA 4 | RNA 3 | RNA 6 | ? |
| mRNA size (bases) | 1600 | 1900 | 1950 | 1190 | ? |
| mRNA molecular weight ($\times 10^6$ daltons) | 0.55 | 0.64 | 0.65 | 0.41 | ? |
| Coding Assignment | NC | F(?) | HA | M | P(?) |

[1]Ten PI3 specific clones could not be classified by the reciprocal hybridization analysis. (NC, nucleocapsid; F, fusion; HA, hemagglutinin; M, matrix; P, phosphoprotein.)

EXAMPLE VI (Northern Blot Analysis)

To determine the corresponding mRNAs for of each of the cDNA clone groups established by reciprocal hybridization, Northern blot analysis was carried out. The cDNA inserts from individual clones in Groups A-D were excised and radiolabeled with $^{32}P$ by nick-translation by the method described in Example V for use as cDNA probes. Messenger RNA from PI-3 virus-infected and mock-infected MDBK cells were denatured using 14% glyoxal and 50% dimethyl sulfoxide in 5% sodium phosphate (pH 6.8) at 50° C. for one hour, and fractionated by electrophoresis in 1% agarose gels. The mRNAs were blot transferred to a nitrocellulose filter by capillary action, using 20x SSC.

After transfer, the filter was baked for 2 hours at 65° C., cooled to room temperature and placed in 5x SSC for 15 minutes. It was then sealed in a bag containing prehybridization buffer (5x Denhardt's Reagent, 5x SSC, 50% formamide, and 100 µg/ml denatured (single strand) salmon sperm DNA) and incubated in a 42° C. water bath for 4 hours. The filter then was cut into strips, each comprising a lane of PI-3 mRNA and a lane of MDBK mRNA. The strips were placed into individual bags containing hybridization buffer (2x Denhardt's, 5x SSC, 50% formamide, 7.5% dextran sulfate, 50 µg/ml denatured salmon sperm DNA and 1.0 mM sodium pyrophosphate). Each strip was hybridized with prepared $^{32}P$-labeled probes, which had been denatured by heating in a boiling water bath for 5 minutes prior to adding to the bag. Hybridization was carried out by incubating in a 42° C. water bath for 20 hours. Following hybridization, the filters were washed with 1.0x SSC and 0.1% SDS (4 washes, 15 minutes each) and then with 0.5x SSC and 0.1% SDS (4 washes, 15 minutes each) at room temperature. Next, they were autoradiographed Tritiated PI-3 mRNA, prepared in Example I, was electrophoresed in a parallel lane blotted to the same nitrocellulose filter and visualized by fluorography using spray EN³Hance (TM) (New England Nuclear) to serve as an internal marker and control. Fluorography was done by exposure to Kodak XAR (TM) film with intensifying screens at −70° C. for 24 to 48 hours, until images were visible.

Individual viral mRNAs were given tentative coding assignments based on the similarities of size relationships to virion proteins and to mRNAs of other paramyxoviruses. In this Example, vesicular stomatitis virus mRNAs were used as markers in order to estimate the molecular weights of the PI-3 mRNAs (Rose, J. et al., "Nucleotide Sequence Complexities, Molecular Weights and Poly (A) Content of Vesicular Stomatitis Virus mRNA Species," *J. of Virology*, Vol. 21, pp. 1105-12 (1975). PI-3 RNAs 4 and 5 migrated very closely and were best resolved when the gels were blot transferred to nitrocellulose rather than dried before fluorography. As shown in Table I, the coding capacity of the six poly-A RNA species correlates roughly with the sizes of the six viral structural proteins and with the estimated total coding capacity of the viral genome. The Group A probe hybridized at a position corresponding to the putative nucleocapsid mRNA, while the Group C probe hybridized at a position corresponding to the putative HA mRNA.

EXAMPLE VII (Hybrid Selection and Translation)

These tentative coding assignments for Groups A and C were confirmed by hybrid selection and in vitro translation of viral mRNA. Plasmid DNA (10 µg) was isolated from PI-3 clones of Groups A and C and purified by CsCl-ethidium bromide centrifugation. The DNA was denatured by heating in 20 µl Tris-HCl (pH 7.5) and 1.0 mM EDTA for 10 minutes to 100° C. and quickly cooling on ice. An equal volume of 1N NaOH was added and the DNA solution incubated at 25° C. for 20 minutes. The solution was neutralized by the addition of 9.0 ml 1.5 M NaCl, 0.15 M sodium citrate and 0.25 M Tris-HCl (pH 8.0). The DNA was immobilized on 2.0 cm diameter nitrocellulose filters (pre-soaked in 3x SSC) by slow filtration using a vacuum manifold. The filters were air-dried for one hour at 25° C. and baked at 80° C. for two hours in a vacuum oven.

After drying, the filters were cut into 0.7 cm strips and placed in a siliconized 30 ml corex tube. A prehybridization solution of 50% (w/v) deionized formamide, 20 mM PIPES (pH 6.4), 0.75 M NaCl, 1.0 mM EDTA, 1% (w/v) SDS, 5.0 µg single-stranded salmon sperm DNA and 5.0 µg of *E. coli* transfer RNA was added. This was incubated for two hours at 37° C. The prehybridization buffer was removed and the strips washed with prehybridization buffer without tRNA and ssDNA.

For hybridizaton, the cut filters were incubated with 50 µg whole cell RNA isolated from viral-infected or mock-infected MDBK cells in a hybridization buffer of 100 µl of 50% (v/v) deionized formamide, 20 mM PIPES (pH 6.4), 0.75 M NaCl, 1.0 mM EDTA, 1% (w/v) SDS and 1.0 mM vanadyl complexes for 5 hours at 50° C. The filters were thoroughly washed with TNE plus 0.5% SDS, and then TNE alone. The filters were transferred to 15 ml corex tubes and 300 µl sterile water added. Elution of the bound mRNA was conducted by boiling in a water bath for one minute. The sample was quick-frozen in liquid nitrogen, and thawed to room temperature. Filters were discarded. The eluted RNA was extracted with phenol, chloroform, isoamyl alcohol and precipitated using ethanol at −70° C. The ethanol precipitated mRNA was collected by centrifugation and lyophilized.

Each eluted hybrid-selected mRNA was translated in cell-free Wheat Germ Extract IVT System (Bethesda Research Laboratories) using $^{35}S$-methionine (New England Nuclear). Viral-specific translation (protein) products were immunoprecipitated by using polyclonal rabbit antisera against purified PI-3 virus. Immune complexes were separated from reaction mixtures by adsorption to protein-A polyacrylamide (Immunobeads (TM), Bio-Rad) as described by Rose, *Nature*, Vol. 279, p.260 (1979). Immunoprecipitated products were released from the protein-A adsorbent by boiling for 5 minutes in 25 µl buffer (5% w/v SDS, 6% v/v 2-mercaptoethanol in water) and electrophoresed in a 10% SDS-polyacrylamide gel system (SDS-PAGE) (Laemmli, *Nature*, Vol. 227 pp. 680-85 (1970)). After electrophoresis, the gels were electroblotted to nitrocellulose paper (Bio-Rad), fluorographed with EN³Hance (TM) spray (New England Nuclear), and autoradiographed for 24 hours to 1 week, until images were visible, at −70° C. using Kodak X-Omat AR (TM) film (Kodak).

As a control, viral mRNA was isolated from bovine PI-3 viral infected cells as described in Example I. The total isolated mRNA was translated according to the in vitro translation procedures described previously in this Example. The translation products (both viral and host) were immunoprecipitated using polyclonal rabbit antisera against purified PI-3 virus as described above to identify viral specific proteins. The proteins identified in this manner are indicated in Table II (Control Polypeptides)

It can be seen that three viral proteins were identified by in vitro translation of the total mRNA, followed by immunoprecipitation. Two of these, the hemagglutinin (HA) and nucleocapsid (NC) proteins, correspond well with viral specific proteins translated by the hybrid-selected mRNAs. That is, the Group A probe hybrid-selected mRNAs which directed the synthesis of a protein with a molecular weight of 65-70,000 daltons (corresponding to 68,000 daltons for the virion nucleocapsid protein and 65-67,000 daltons for the control group protein). The Group C probe hybrid-selected mRNAs which directed the synthesis of a protein with a molecular weight of 60,000 daltons (corresponding to 69,000 daltons for the virion hemagglutinin protein and 60,000 daltons for the control group protein). A 31,000 dalton protein was identified in the control group which corresponds with the 35,000 dalton virion matrix protein. No viral-specific polypeptides were detected in wheat germ extracts programmed with RNA from mock-infected cells.

TABLE II

| (Molecular Weights[1] of Bovine PI-3 Virus Polypeptides) | | | |
|---|---|---|---|
| Polypeptide Designation | Virion Polypeptides | Control Polypeptides | Hybrid-Selected Polypeptides |
| L | 180,000 | ND[2] | ND |
| P | 79,000 | ND | ND |
| HA[3] | 69,000 | 60,000 | 60,000 |
| NC[4] | 68,000 | 65-67,000 | 65-70,000 |
| F | 55,000 | ND | ND |
| M[4] | 35,000 | 31,000 | ND |

[1]Molecular weights are expressed in daltons.
[2]ND = "not detected"
[3]The difference in molecular weights between the virion HA polypeptides and the in vitro translated HA polypeptides is due to the lack of glycosylation in the in vitro products.
[4]Nucleocapsid (NC) and matrix (M) proteins are nonglycosylated and thus exhibit less viariability in molecular weight as determined by SDS-PAGE gels.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A synthetic gene or DNA fragment characterized in that it:
   (a) codes for a bovine parainfluenza type-3 viral protein, and
   (b) comprises a double-stranded DNA gene which is a copy of the viral RNA gene coding for said protein.

2. The synthetic gene of claim 1 which codes for bovine parainfluenza type-3 hemagglutinin.

3. The DNA sequence of the synthetic gene of claim 2 which begins with an initiation codon, ends with a termination of stop codon, and comprises the nucleotide sequence of FIG. 1.

4. The DNA sequence of the synthetic gene of claim 2 which codes for a polypeptide comprising the amino acid sequence of FIG. 4.

5. The synthetic gene of claim 1 which codes for bovine parainfluenza type-3 structural fusion protein.

6. The plasmid pBR322 comprising the double-stranded DNA gene of claim 1.

7. The host cell E. coli comprising the double-stranded DNA gene of claim 1.

8. A synthetic gene for a bovine parainfluenza viral target protein, which protein is coded for in the natural state by a gene located on the non-segmented minus strand viral genome of the bovine parainfluenza type-3 virus, produced by:
   (a) isolating a population of mRNA comprising the genes coding for said viral protein,
   (b) constructing double-stranded mRNA/cDNA hybrids from said population of mRNA using the enzyme reverse transcriptase and oligodeoxynucleotide primer molecules,
   (c) digesting or removing the mRNA strands of said hybrids,
   (d) producing substantially completely double-stranded cDNA molecules from the single-stranded cDNA remaining after step (c), using a DNA polymerase, and
   (e) trimming single-stranded end portions of said substantially completely double-stranded cDNA molecules using a single-strand specific nuclease.

9. The synthetic gene of claim 8 which comprises the nucleotide sequence of FIG. 1.

10. The synthetic gene of claim 8 which codes for a polypeptide comprising the amino acid sequence of FIG. 4.

11. The plasmid pBR322 comprising the synthetic gene of claim 8.

12. The hose cell E. coli transformed with the plasmid of claim 11 and capable of expressing the protein of the synthetic gene contained therein.

* * * * *

UNITED STATES PATENT AND TRADEMARK OFFICE
CERTIFICATE OF CORRECTION

PATENT NO. : 4,743,553

DATED : May 10, 1988

INVENTOR(S) : John M. Rice

It is certified that error appears in the above-identified patent and that said Letters Patent is hereby corrected as shown below:

```
Col. 2, line 29:    "prooes" should be --probes--.
Col. 8, line 5:     "Tnis" should be --This--.
Col. 15, line 27:   "bufter" should be --buffer--.
Col. 15, lines 39-40: "autoradiographed" should
        be --autoradiographed.--.

Claim 12, Col. 18, line 53:   "hose" should be --host--.
```

Signed and Sealed this

First Day of June, 1993

Attest:

MICHAEL K. KIRK

Attesting Officer

Acting Commissioner of Patents and Trademarks